United States Patent
Chaggares

(10) Patent No.: US 10,265,047 B2
(45) Date of Patent: Apr. 23, 2019

(54) HIGH FREQUENCY ULTRASOUND TRANSDUCER HAVING AN ULTRASONIC LENS WITH INTEGRAL CENTRAL MATCHING LAYER

(71) Applicant: FUJIFILM SonoSite, Inc., Bothell, WA (US)

(72) Inventor: Nicholas Christopher Chaggares, Whitby (CA)

(73) Assignee: FUJIFILM SONOSITE, INC., Bothell, WA (US)

( * ) Notice: Subject to any disclaimer, the term of this patent is extended or adjusted under 35 U.S.C. 154(b) by 825 days.

(21) Appl. No.: 14/656,602

(22) Filed: Mar. 12, 2015

(65) Prior Publication Data
US 2015/0257734 A1  Sep. 17, 2015

Related U.S. Application Data

(60) Provisional application No. 61/952,086, filed on Mar. 12, 2014.

(51) Int. Cl.
| A61B 8/00 | (2006.01) |
| G10K 11/30 | (2006.01) |
| B06B 1/06 | (2006.01) |

(52) U.S. Cl.
CPC ............ *A61B 8/4272* (2013.01); *B06B 1/067* (2013.01); *G10K 11/30* (2013.01); *Y10T 156/10* (2015.01)

(58) Field of Classification Search
None
See application file for complete search history.

(56) References Cited

U.S. PATENT DOCUMENTS

| 4,240,090 A | 12/1980 | Hughes et al. |
| 4,387,720 A | 6/1983 | Miller et al. |
| 4,484,820 A | 11/1984 | Rosencwaig |
| 4,523,122 A | 6/1985 | Tone et al. |
| 4,651,850 A | 3/1987 | Matsuo |
| 4,672,963 A | 6/1987 | Barken |
| 4,699,150 A | 10/1987 | Kawabuchi et al. |
| 4,856,335 A | 8/1989 | Tornberg |
| 5,050,128 A | 9/1991 | Saitoh et al. |
| 5,070,733 A | 12/1991 | Nagata et al. |

(Continued)

FOREIGN PATENT DOCUMENTS

| CN | 1650794 A | 8/2005 |
| CN | 101247754 A | 8/2008 |

(Continued)

OTHER PUBLICATIONS

C-Lec Plastics Inc., "Rexolite, High Voltage, High Performance Plastic: Rexolite Specifications". Copyright 2015. pp. 1-3. (Discloses inherent characteristics of Rexolite).*

(Continued)

*Primary Examiner* — James Kish
(74) *Attorney, Agent, or Firm* — Baker Botts L.L.P.

(57) ABSTRACT

High frequency ultrasound transducers configured for use with high frequency ultrasound diagnostic imaging systems are disclosed herein. In one embodiment, an ultrasound transducer includes a concave lens having an average thickness in a center portion that that is substantially equal to an odd multiple a ¼-wavelength of the center frequency of the ultrasound transducer.

13 Claims, 3 Drawing Sheets

(56) References Cited

U.S. PATENT DOCUMENTS

| | | |
|---|---|---|
| 5,136,172 A | 8/1992 | Nakata et al. |
| 5,235,553 A | 8/1993 | Garlick et al. |
| 5,265,612 A | 11/1993 | Sarvazyan et al. |
| 5,353,798 A | 10/1994 | Sieben |
| 5,365,024 A | 11/1994 | Hasegawa et al. |
| 5,553,035 A | 9/1996 | Seyed-Bolorforosh et al. |
| 5,577,507 A | 11/1996 | Snyder et al. |
| 5,713,356 A | 2/1998 | Kruger |
| 5,718,231 A | 2/1998 | Dewhurst et al. |
| 5,800,350 A | 9/1998 | Coppleson et al. |
| 5,840,023 A | 11/1998 | Oraevsky et al. |
| 5,971,925 A | 10/1999 | Hossack et al. |
| 5,991,693 A | 11/1999 | Zalewski |
| 6,102,857 A | 8/2000 | Kruger et al. |
| 6,104,942 A | 8/2000 | Kruger |
| 6,182,341 B1 | 2/2001 | Talbot et al. |
| 6,183,578 B1 | 2/2001 | Ritter et al. |
| 6,194,814 B1 | 2/2001 | Hanafy et al. |
| 6,216,025 B1 | 4/2001 | Kruger |
| 6,246,898 B1 | 6/2001 | Vesely et al. |
| 6,292,682 B1 | 9/2001 | Kruger |
| 6,443,900 B2 | 9/2002 | Adachi et al. |
| 6,490,470 B1 | 12/2002 | Kruger |
| 6,498,942 B1 | 12/2002 | Esenaliev et al. |
| 6,519,376 B2 | 2/2003 | Biagi et al. |
| 6,551,247 B2 | 4/2003 | Saito et al. |
| 6,567,688 B1 | 5/2003 | Wang |
| 6,633,774 B2 | 10/2003 | Kruger |
| 6,645,144 B1 | 11/2003 | Wen et al. |
| 6,851,392 B2 | 2/2005 | Zan et al. |
| 6,979,282 B1 | 12/2005 | Mangano |
| 7,052,460 B2 | 5/2006 | Liu et al. |
| 7,133,713 B2 | 11/2006 | Zan |
| 7,139,676 B2 | 11/2006 | Barford |
| 7,230,368 B2 | 6/2007 | Lukacs et al. |
| 7,245,789 B2 | 7/2007 | Bates et al. |
| 7,266,407 B2 | 9/2007 | Li et al. |
| 7,367,948 B2 | 5/2008 | O'Donnell et al. |
| 7,426,904 B2 | 9/2008 | Zan et al. |
| 7,447,388 B2 | 11/2008 | Bates et al. |
| 7,713,200 B1 | 5/2010 | Sarvazyan et al. |
| 7,750,536 B2 | 7/2010 | Chaggares et al. |
| 7,774,042 B2 | 8/2010 | Kruger |
| 7,798,705 B2 | 9/2010 | Burgholzer et al. |
| 7,808,156 B2 | 10/2010 | Chaggares et al. |
| 8,078,256 B2 | 12/2011 | Zan |
| 8,343,289 B2 | 1/2013 | Chaggares et al. |
| 8,529,454 B2 | 9/2013 | Chen |
| 8,847,467 B2 | 9/2014 | Chaggares et al. |
| 9,520,119 B2 | 12/2016 | Chaggares et al. |
| 9,791,417 B2 | 10/2017 | Irisawa et al. |
| 2001/0041842 A1 | 11/2001 | Eberle et al. |
| 2001/0055435 A1 | 12/2001 | Biagi et al. |
| 2002/0007118 A1 | 1/2002 | Adachi et al. |
| 2002/0035327 A1 | 3/2002 | Kruger |
| 2002/0111620 A1 | 8/2002 | Cooper et al. |
| 2002/0193678 A1 | 12/2002 | Kruger |
| 2003/0032884 A1 | 2/2003 | Smith et al. |
| 2003/0069491 A1 | 4/2003 | Kruger |
| 2003/0187356 A1 | 10/2003 | Wakabayashi et al. |
| 2003/0203304 A1 | 10/2003 | Katagiri et al. |
| 2004/0000847 A1 | 1/2004 | Ladabaum et al. |
| 2004/0040379 A1 | 3/2004 | O'Donnell et al. |
| 2004/0054287 A1 | 3/2004 | Stephens |
| 2004/0067000 A1 | 4/2004 | Bates et al. |
| 2004/0095045 A1 | 5/2004 | Baumgartner |
| 2004/0122319 A1 | 6/2004 | Mehi et al. |
| 2004/0127783 A1 | 7/2004 | Kruger |
| 2004/0215072 A1 | 10/2004 | Zhu |
| 2004/0236219 A1 | 11/2004 | Liu et al. |
| 2005/0004458 A1 | 1/2005 | Kanayama et al. |
| 2005/0070803 A1 | 3/2005 | Cullum et al. |
| 2005/0101854 A1 | 5/2005 | Larson et al. |
| 2005/0107692 A1 | 5/2005 | Li et al. |
| 2005/0127793 A1 | 6/2005 | Baumgartner et al. |
| 2005/0187471 A1 | 8/2005 | Kanayama et al. |
| 2005/0240102 A1 | 10/2005 | Rachlin et al. |
| 2005/0272183 A1 | 12/2005 | Lukacs et al. |
| 2006/0055486 A1 | 3/2006 | Nakatsuka et al. |
| 2006/0184042 A1 | 8/2006 | Wang et al. |
| 2007/0016071 A1 | 1/2007 | Eberle et al. |
| 2007/0049829 A1* | 3/2007 | Kaminski ............ B06B 1/0677 600/459 |
| 2007/0093702 A1 | 4/2007 | Yu et al. |
| 2007/0121697 A1 | 5/2007 | Burgholzer et al. |
| 2007/0133925 A1 | 6/2007 | Bates et al. |
| 2007/0182287 A1 | 8/2007 | Lukacs et al. |
| 2007/0205697 A1 | 9/2007 | Chaggares et al. |
| 2007/0205698 A1 | 9/2007 | Chaggares et al. |
| 2007/0239001 A1 | 10/2007 | Mehi et al. |
| 2007/0249916 A1 | 10/2007 | Pesach et al. |
| 2008/0108867 A1 | 5/2008 | Zhou |
| 2008/0123083 A1 | 5/2008 | Wang et al. |
| 2008/0156577 A1 | 7/2008 | Dietz et al. |
| 2008/0173093 A1 | 7/2008 | Wang et al. |
| 2008/0194965 A1 | 8/2008 | Sliwa et al. |
| 2008/0221647 A1 | 9/2008 | Chamberland et al. |
| 2009/0024038 A1 | 1/2009 | Arnold |
| 2009/0024040 A1 | 1/2009 | Cespedes |
| 2009/0048489 A1 | 2/2009 | Igarashi et al. |
| 2009/0054763 A1 | 2/2009 | Wang et al. |
| 2009/0105588 A1 | 4/2009 | Emelianov et al. |
| 2009/0112098 A1* | 4/2009 | Vaezy .................... A61B 8/546 600/459 |
| 2009/0124902 A1 | 5/2009 | Herrmann |
| 2009/0187099 A1 | 7/2009 | Burcher |
| 2009/0227997 A1 | 9/2009 | Wang et al. |
| 2009/0240149 A1 | 9/2009 | Peyman |
| 2009/0281431 A1 | 11/2009 | Phillips et al. |
| 2009/0324890 A1 | 12/2009 | Wu et al. |
| 2010/0016717 A1 | 1/2010 | Dogra et al. |
| 2010/0028261 A1 | 2/2010 | Emelianov et al. |
| 2010/0037695 A1 | 2/2010 | Tsujita et al. |
| 2010/0041987 A1 | 2/2010 | Manohar et al. |
| 2010/0049044 A1 | 2/2010 | Burcher |
| 2010/0053618 A1 | 3/2010 | Nakajima et al. |
| 2010/0087732 A1 | 4/2010 | Eberle et al. |
| 2010/0094134 A1 | 4/2010 | Zhu et al. |
| 2010/0156244 A1* | 6/2010 | Lukacs ................ B06B 1/0622 310/335 |
| 2010/0196278 A1 | 8/2010 | Tomida |
| 2010/0208965 A1 | 8/2010 | Jiang et al. |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0249570 A1 | 9/2010 | Carson et al. |
| 2010/0268042 A1 | 10/2010 | Wang et al. |
| 2010/0268058 A1 | 10/2010 | Chen |
| 2010/0298688 A1 | 11/2010 | Dogra et al. |
| 2010/0298689 A1 | 11/2010 | Wang |
| 2010/0331662 A1 | 12/2010 | Fukutani et al. |
| 2011/0021924 A1 | 1/2011 | Sethuraman et al. |
| 2011/0044516 A1 | 2/2011 | Li et al. |
| 2011/0045607 A1 | 2/2011 | Li et al. |
| 2011/0054292 A1 | 3/2011 | Hirson et al. |
| 2011/0054294 A1 | 3/2011 | Kruger |
| 2011/0066023 A1 | 3/2011 | Kanayama et al. |
| 2011/0081294 A1 | 4/2011 | Fukui et al. |
| 2011/0088477 A1 | 4/2011 | Someda et al. |
| 2011/0117023 A1 | 5/2011 | Yamauchi et al. |
| 2011/0128816 A1 | 6/2011 | Baba et al. |
| 2011/0144496 A1 | 6/2011 | Li et al. |
| 2011/0144502 A1 | 6/2011 | Zhou et al. |
| 2011/0262750 A1 | 10/2011 | Taima |
| 2012/0029353 A1* | 2/2012 | Slayton .................. A61N 7/02 600/439 |
| 2013/0190591 A1 | 7/2013 | Hirson et al. |
| 2013/0289381 A1 | 10/2013 | Oraevsky et al. |
| 2014/0345385 A1 | 11/2014 | Irisawa et al. |
| 2015/0108874 A1 | 4/2015 | Chaggares et al. |

(56) References Cited

U.S. PATENT DOCUMENTS

| | | | |
|---|---|---|---|
| 2015/0173625 A1 | 6/2015 | Chaggares et al. | |
| 2017/0144195 A1 | 5/2017 | Chaggares et al. | |

FOREIGN PATENT DOCUMENTS

| | | | |
|---|---|---|---|
| CN | 101268953 A | | 9/2008 |
| CN | 101442940 A | | 5/2009 |
| CN | 103209643 A | | 7/2013 |
| EP | 0413330 A2 | | 2/1991 |
| EP | 0413330 A3 | | 2/1991 |
| EP | 0413330 B1 | | 2/1991 |
| EP | 1602331 A1 | | 12/2005 |
| EP | 1935346 A1 | | 6/2008 |
| EP | 2110076 A1 | | 10/2009 |
| EP | 2180352 A1 | | 4/2010 |
| JP | 54013370 | | 1/1979 |
| JP | 56086598 | | 7/1981 |
| JP | 58171665 | | 10/1983 |
| JP | 61172546 | | 8/1986 |
| JP | 61278297 | | 12/1986 |
| JP | 62097245 A | | 5/1987 |
| JP | 0283481 | | 3/1990 |
| JP | 02260999 | | 10/1990 |
| JP | 04040099 | | 2/1992 |
| JP | 07159379 A | | 6/1995 |
| JP | 07159381 A | | 6/1995 |
| JP | 09107594 | | 4/1997 |
| JP | 11206759 A | | 8/1999 |
| JP | 2000292416 A | | 10/2000 |
| JP | 2001069594 | | 3/2001 |
| JP | 2003295496 A | | 10/2003 |
| JP | 3495069 B2 | | 2/2004 |
| JP | 2004351023 A | | 12/2004 |
| JP | 2005198261 | | 7/2005 |
| JP | 2005218684 A | | 8/2005 |
| JP | 3745157 B2 | | 2/2006 |
| JP | 2006208050 A | | 8/2006 |
| JP | 2006242816 A | | 9/2006 |
| JP | 3894024 B2 | | 3/2007 |
| JP | 2007097654 A | | 4/2007 |
| JP | 2009031268 A | | 2/2009 |
| JP | 3156362 U | | 12/2009 |
| JP | 2010022816 A | | 2/2010 |
| JP | 2010057730 A | | 3/2010 |
| JP | 2010075681 A | | 4/2010 |
| JP | 2010088627 | | 4/2010 |
| JP | 2010104816 | | 5/2010 |
| JP | 2010136887 A | | 6/2010 |
| JP | 2011005042 | | 1/2011 |
| KR | 101222198 B1 | | 1/2013 |
| KR | 20130123347 A | | 11/2013 |
| TW | I240990 B | | 10/2005 |
| TW | I328972 B | | 8/2010 |
| TW | M458203 U | | 8/2013 |
| WO | 1994014379 A1 | | 7/1994 |
| WO | 1998014118 A1 | | 4/1998 |
| WO | 2000022987 A2 | | 4/2000 |
| WO | 2000045707 A2 | | 8/2000 |
| WO | 2001010298 | | 2/2001 |
| WO | 2004020986 | | 3/2004 |
| WO | 2004032746 A2 | | 4/2004 |
| WO | 2004042382 | | 5/2004 |
| WO | 2005048840 A1 | | 6/2005 |
| WO | 2005104210 | | 11/2005 |
| WO | 2006007611 A1 | | 1/2006 |
| WO | 2006061829 A1 | | 6/2006 |
| WO | 2007072490 A1 | | 6/2007 |
| WO | 2007084981 A2 | | 7/2007 |
| WO | 2007100937 A2 | | 9/2007 |
| WO | 2007103143 | | 9/2007 |
| WO | 2007103144 | | 9/2007 |
| WO | 2007117572 A2 | | 10/2007 |
| WO | 2007084981 A3 | | 11/2007 |
| WO | 2007148239 A2 | | 12/2007 |
| WO | 2008011112 | | 1/2008 |
| WO | 2007148239 A3 | | 2/2008 |
| WO | 2008066962 A1 | | 6/2008 |
| WO | 2008067438 A2 | | 6/2008 |
| WO | 2008075299 A1 | | 6/2008 |
| WO | 2008075961 A2 | | 6/2008 |
| WO | 2007100937 A3 | | 7/2008 |
| WO | 2008067438 A3 | | 7/2008 |
| WO | 2007117572 A3 | | 8/2008 |
| WO | 2008097527 | | 8/2008 |
| WO | 2008100386 A2 | | 8/2008 |
| WO | 2008101019 A2 | | 8/2008 |
| WO | 2008103982 A2 | | 8/2008 |
| WO | 2008100386 A3 | | 10/2008 |
| WO | 2008103982 A3 | | 10/2008 |
| WO | 2008101019 A3 | | 11/2008 |
| WO | 2008143200 | | 11/2008 |
| WO | 2008075961 A3 | | 12/2008 |
| WO | 2009011884 A1 | | 1/2009 |
| WO | 2009011934 A1 | | 1/2009 |
| WO | 2009045885 A2 | | 4/2009 |
| WO | 2009055705 A2 | | 4/2009 |
| WO | 2009063424 A1 | | 5/2009 |
| WO | 2009064030 A1 | | 5/2009 |
| WO | 2009045885 A3 | | 6/2009 |
| WO | 2009055705 A3 | | 6/2009 |
| WO | 2009073979 A1 | | 6/2009 |
| WO | 2009076427 | | 6/2009 |
| WO | 2009103502 A1 | | 8/2009 |
| WO | 2009154298 A1 | | 12/2009 |
| WO | 2009154963 A1 | | 12/2009 |
| WO | 2009158146 | | 12/2009 |
| WO | 2010009412 A2 | | 1/2010 |
| WO | 2009158146 A3 | | 3/2010 |
| WO | 2010027095 A1 | | 3/2010 |
| WO | 2010030817 A1 | | 3/2010 |
| WO | 2010039950 A1 | | 4/2010 |
| WO | 2010045421 A2 | | 4/2010 |
| WO | 2010048623 A2 | | 4/2010 |
| WO | 2010048623 A8 | | 4/2010 |
| WO | 2010067608 A1 | | 6/2010 |
| WO | 2010045421 A3 | | 7/2010 |
| WO | 2010086861 A1 | | 8/2010 |
| WO | 2010107930 A1 | | 9/2010 |
| WO | 2010107933 A1 | | 9/2010 |
| WO | 2010048623 A9 | | 10/2010 |
| WO | 2010048623 A3 | | 11/2010 |
| WO | 2010127199 A2 | | 11/2010 |
| WO | 2010135469 A1 | | 11/2010 |
| WO | 2011000389 A1 | | 1/2011 |
| WO | 2010009412 A3 | | 2/2011 |
| WO | 2011012274 A1 | | 2/2011 |
| WO | 2011035279 A2 | | 3/2011 |
| WO | 2011053931 A2 | | 5/2011 |
| WO | 2011074102 A1 | | 6/2011 |
| WO | 2011137385 | | 11/2011 |
| WO | 2013121743 A1 | | 8/2013 |
| WO | 2013145764 A1 | | 10/2013 |
| WO | 2015095721 | | 6/2015 |
| WO | 2015138796 | | 9/2015 |

OTHER PUBLICATIONS

U.S. Appl. No. 61/174,571, filed May 1, 2009, Hirson et al.
Japan Patent Office, Official Action, JP Patent Application 2013-508293, dated Jan. 26, 2015, 7 pages.
European Patent Office, Supplementary European Search Report, EP Patent Application 11775660.1, dated Dec. 16, 2013, 8 pages.
International Searching Authority, International Search Report, PCT Application PCT/US2011/034640, dated Aug. 8, 2011, 2 pages.
International Search Authority, Written Opinion, PCT Application PCT/US2011/034640, dated Aug. 8, 2011, 8 pages.
Oraevsky, A.A. et al. "Laser-based optoacoustic imaging in biological tissues." Proc. SPIE vol. 2134A, p. 122-128, Laser-Tissue Interaction V, Steven L. Jacques, Ed., Aug. 1994.
State Intellectual Property Office, First Office Action, Chinese Patent Application CN 201180031854.0, dated Sep. 28, 2014, 13 pages.

(56) References Cited

OTHER PUBLICATIONS

State Intellectual Property Office, Second Office Action, Chinese Patent Application CN 201180031854.0, dated May 18, 2015, 4 pages.
Farquhar and Steinwall. "Elastic Properties of Filled Epoxy Encapsulants," EEP vol. 10-2, Advances in Electronic Packaging, ASME, 1995, pp. 707-711.
Grewe, Gururafa, Newnham, and Shrout. "Acoustic Properties of Particle/Polymer Composites for Transducer Backing Applications," *IEEE Trans. on Ultrasonics, Ferroelectrics and Frequency Control*, 37(6): 506-514, 1990.
Ritter, Shung, Geng, Lopath, Tutwiler, and Shrout. "Composite ultrasound transducer arrays for operation above 20 MHz." Proceedings of SPIE, vol. 3664 Medical Imaging 1999: Ultrasonic Transducer Engineering, K.Kirk Shung, editor, pp. 67-75, Jun. 1999.
Selfridge. "Approximate Material Properties in Isotropic Materials," *IEE Trans Sonics and Ultrasonics*, vol. SU-32, No. 3, May 1985, pp. 381-384.
Wang, Ritter, Cao, and Shung. "Passive Materials for High Frequency Ultrasound Transducers," SPIE Conf. on Ultrasonic Transducer Engineering, San Diego, California, SPIE vol. 3664, Feb. 1999, 8 pages.
Callens, D. et al. "Matching ultrasonic transducer using two matching layers where one of them is glue," NDT & E International, Butterworth-Heinemann, Oxford, GB, Dec. 1, 2004, vol. 37, No. 8, pp. 591-596.
International Search Report and Written Opinion, PCT Patent Application PCT/US2007/05300, dated Feb. 14, 2008, 7 pages.
International Search Report and Written Opinion, PCT Patent Application PCT/US2007/05301, dated Feb. 20, 2008, 7 pages.
First Office Action for Chinese Patent Application No. CN200780016016.X, dated Jun. 8, 2010, 13 pages.
Second Office Action for Chinese Patent Application No. CN200780016016.X, dated Jan. 12, 2011, 16 pages.
Third Office Action for Chinese Patent Application No. CN200780016016.X, dated Jul. 6, 2011, 3 pages.
Fourth Office Action for Chinese Patent Application No. CN200780016016.X, dated Oct. 26, 2011, 3 pages.
Extended Search Report, European Patent Application No. EP07752028.6, dated Mar. 29, 2012, 6 pages.
Notice of Reasons for Rejection, Japanese Patent Application No. JP2008-557385, dated Oct. 6, 2011, 6 pages.
Canadian Intellectual Property Office, Examiner's Report, CA Patent Application 2,644,224, dated Jan. 7, 2014, 2 pages.
Canadian Intellectual Property Office, Examiner's Report, CA Patent Application 2,644,224, dated Oct. 6, 2014, 4 pages.
Japan Patent Office, Final Rejection, JP Patent Application 2008-557385, dated Jan. 9, 2013, 5 pages; with English translation.
Japan Patent Office, Final Rejection, JP Patent Application 2013-099049, dated Oct. 29, 2014, 6 pages; with English translation.
Japan Patent Office, Notice of Reasons for Rejection, JP Patent Application 2008-557385, dated Aug. 6, 2012, 7 pages; with English translation.
Japan Patent Office, Notice of Reasons for Rejection, JP Patent Application 2012-087397, dated Aug. 6, 2014, 11 pages; with English translation.
Japan Patent Office, Notice of Reasons for Rejection, JP Patent Application 2012-087397, dated Dec. 17, 2013, 7 pages; with English translation.
Japan Patent Office, Notice of Reasons for Rejection, JP Patent Application 2013-099049, dated Dec. 17, 2013, 6 pages; with English translation.
International Searching Authority, International Search Report and Written Opinion, International Application PCT/US2014/071533, dated Apr. 20, 2015, 19 pages.
International Searching Authority, International Search Report and Written Opinion, International Application PCT/US2015/020279, dated Jun. 19, 2015, 14 pages.
Taiwan Intellectual Property Office, Examination Opinion, TW Patent Application 103144411, dated Nov. 15, 2016, 24 pages (with English translation).
Japanese Patent Office, Notice of Final Rejection, JP Patent Application 2015-219452, dated Apr. 2, 2018, 16 pages; with English translation.
Japanese Patent Office, Office Action, JP Patent Application 2015-219452, dated May 19, 2017, 13 pages; with English translation.
European Patent Office, Extended European Search Report, EP Patent Application 15762059.2, dated Nov. 30, 2017, 9 pages.
European Patent Office, Partial European Search Report, EP Patent Application 14870691.4, dated Jan. 19, 2018, 12 pages.
Taiwan Intellectual Property Office, Examination Opinion, TW Patent Application 104107859, dated May 7, 2018, 18 pages (with English translation).

\* cited by examiner

HIGH FREQUENCY ULTRASOUND TRANSDUCER HAVING AN ULTRASONIC LENS WITH INTEGRAL CENTRAL MATCHING LAYER

TECHNICAL FIELD

The disclosed technology generally relates to the fields of ultrasonic transducers and medical diagnostic imaging. More specifically, the disclosed technology relates to high frequency ultrasonic transducers and acoustic lenses configured for use therewith.

PATENTS AND PATENT APPLICATIONS INCORPORATED BY REFERENCE

The following patents are also incorporated by reference herein in their entireties: U.S. Pat. No. 7,052,460, titled "SYSTEM FOR PRODUCING AN ULTRASOUND IMAGE USING LINE-BASED IMAGE RECONSTRUCTION," and filed Dec. 15, 2003; U.S. Pat. No. 7,255,648, titled "HIGH FREQUENCY, HIGH FRAME-RATE ULTRASOUND IMAGING SYSTEM," and filed Oct. 10, 2003; U.S. Pat. No. 7,230,368, titled "ARRAYED ULTRASOUND TRANSDUCER," and filed Apr. 20, 2005; U.S. Pat. No. 7,808,156, titled "ULTRASONIC MATCHING LAYER AND TRANSDUCER," and filed Mar. 2, 2006; U.S. Pat. No. 7,901,358, titled "HIGH FREQUENCY ARRAY ULTRASOUND SYSTEM," and filed Nov. 2, 2006; and U.S. Pat. No. 8,316,518, titled "METHODS FOR MANUFACTURING ULTRASOUND TRANSDUCERS AND OTHER COMPONENTS," and filed Sep. 18, 2009.

BRIEF DESCRIPTION OF THE DRAWINGS

The invention may be more completely understood in consideration of the accompanying drawings, which are incorporated in and constitute a part of this specification, and together with the description, serve to illustrate the disclosed technology.

DETAILED DESCRIPTION

Figure 1:
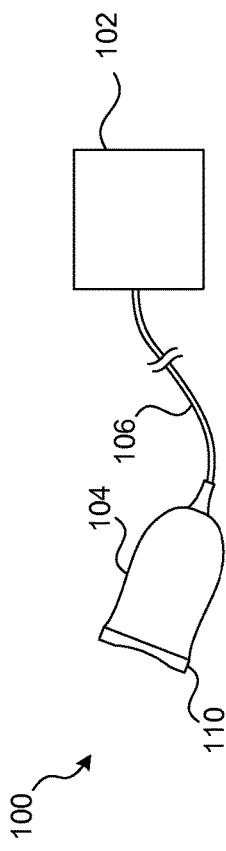
FIG. 1 is a schematic view of an ultrasound imaging system configured in accordance with one or more embodiments of the disclosed technology.

Ultrasonic transducers provide a means for converting electrical energy into acoustic energy and vice versa. When the electrical energy is in the form of a radio frequency (RF) signal, a transducer can produce ultrasonic signals with the same frequency characteristics as the driving electrical RF signal. Conventional clinical ultrasound transducers are typically operated at center frequencies ranging from less than 1 Megahertz (MHz) to about 10 MHz. Ultrasound in the frequency spectrum of 1-10 MHz generally provides a means of imaging biological tissue with a resolution ranging from several millimeters to generally greater than 150 microns and at depths from a few millimeters to greater than 10 centimeters.

In contrast, high frequency ultrasonic (HFUS) transducers are generally ultrasonic transducers with center frequencies above 15 MHz and ranging to over 60 MHz (e.g., 15 MHz, 20 MHz, 25 MHz, 30 MHz, 40 MHz, 50 MHz, 60 MHz). HFUS transducers provide higher resolution than transducers that operate at lower frequencies (e.g., less than 15 MHz.) while limiting a maximum depth of penetration. As a result, HFUS transducers can image biological tissue at depths ranging from, for example, a fraction of a millimeter (e.g., 0.25 mm, 0.5 mm, 0.75 mm) to 3 cm or greater (e.g., 4 cm) with resolutions ranging, for example, from about 20 microns to about 200 microns.

For transducers operating at frequencies less than 10 MHz, for example, a wide variety of lens materials are available to produce convex lenses that are substantially acoustically impedance-matched to a medium (e.g., tissue in a subject) to be imaged. Acoustic energy received at these transducers is typically almost completely transmitted through the lens material to be received by the transducer, with almost no energy reflected back into the medium, and thus no multipath artifacts are created. In addition, one skilled in the art will understand that a well-designed transducer, having a well matched lens material will not exhibit multiple reflections within the lens itself. In the case of HFUS transducers, however, very few materials are suitable for constructing acoustic lenses due to significantly higher acoustic attenuation. As those of ordinary skill in the art will appreciate, acoustic attenuation in polymers tends to increase exponentially with frequency. Accordingly, an acoustic attenuation of ultrasound energy at 20 MHz in a polymer can be an order of magnitude (e.g., 10 times greater, 20 times greater, 100 times greater) than an acoustic attenuation of ultrasound energy of 10 MHz and below in the same polymer.

There can be many challenges associated with fabricating HFUS transducers that do not arise when working with traditional clinical ultrasonic transducers that operate at frequencies below about 10 MHz. Those of ordinary skill in the art will appreciate that structures (e.g., transducer layers, matching layers, lenses) associated with an ultrasound transducer generally scale in a manner that is inversely proportional to an operating frequency of the transducer. For example, a 50 MHz transducer will have structures about 10 times smaller than a 5 MHz transducer. In many cases, materials or techniques used with lower frequency transducers (e.g., less than about 10 MHz.) cannot be scaled down to sizes and/or shapes suitable for use in HFUS transducers. Accordingly, new technologies may need to be developed or adapted in the fabrication of HFUS transducers. In other cases, entirely new requirements exist when dealing with the higher radio frequency electronic and acoustic signals associated with HFUS transducers.

Conventional HFUS transducers typically include hard plastic acoustic lenses shaped and/or formed into concave lenses in order to focus an elevation dimension of the transducer. Suitable HFUS lens materials may include, for example, polymethylpentene (e.g., TPX®), cross-linked polystyrene (e.g., Rexolite®), and polybenzimidazole (e.g., Celazole®), all of which have relatively low attenuation at frequencies greater than about 15 MHz. Acoustic lenses made from materials suited for HFUS use, however, may also have acoustic impedances significantly or substantially different (e.g., 10% different, 25% different, 50% different) from an acoustic impedance of a subject to be imaged. The resulting acoustic impedance mismatch (e.g., a difference of 0.1 MRayl, 0.3 MRayl, 0.5 MRayl, 1 MRayl, 2 MRayls) between the lens and the subject can cause multipath imaging artifacts when ultrasound energy is transmitted from the transducer and received at the transducer to form an ultrasound image. An acoustic impedance mismatch at the front of the lens with respect to the coupling medium or the subject can also result in intra-lens reflections and/or lens reverberation artifacts that can degrade the axial resolution of the ultrasound transducer.

The multipath or multi-bounce artifacts can cause a ghost image of bright specular reflectors appearing an equal depth below the true image of the specular reflector. A skin line of a subject, for example, may be imaged at a depth of 4 mm in the image and cause a multipath artifact at a depth of 8 mm. Those of ordinary skill in the art will appreciate that such an artifact may be produced when ultrasonic energy emitted from the transducer strikes a strong specular reflector (e.g., a skin line of a subject) roughly normal to the path of the ultrasound. A portion (e.g., 5%, 10%) of the emitted ultrasonic energy may be reflected back from the specular reflector toward the transducer lens, whereupon a second reflection may occur if the lens is not substantially acoustically matched to the transmission medium (e.g., gel, water). The second reflection may then propagate back to the specular reflector a second time, where again, a specular reflection occurs and acoustic energy is once again received by the transducer. A cascade of such reflections can cause a series of multipath artifacts to appear in an ultrasound image. Such partial reflections can occur repeatedly until no significant energy remains in the reflections. One approach to mitigating imaging artifacts may include positioning an acoustic matching layer on an outer surface of an acoustic lens. Lenses having matching layers on their outer surfaces, however, can be very difficult to fabricate and, in many cases, are impractical for use with ultrasound transducers that operate at higher frequencies (e.g., greater than about 15 MHz.).

Lens reverberation artifacts caused by, for example, intra-lens multiple reflections can be similar to the multipath artifacts described above. Intra-lens reflections, however, occur entirely within the lens material and may be caused by an acoustic mismatch between the outer surface of the lens and the acoustic coupling medium or the subject being imaged. A partial echo is produced at the front face of the lens as the acoustic pulse exits the transducer and enters the subject. This echo can then reverberate between any internal acoustic mismatch in the transducer acoustic stack, such as the back surface of the lens for example. As those of ordinary skill in the art will appreciate, every effort will be made to acoustically match the back surface of the lens to the acoustic stack of the transducer, typically through the use of some form of acoustic matching layer. However, due to the low attenuation of HFUS lens materials, even a small reflection from the back surface/stack interface can give rise to a lens reverb artifact. The effect of the lens reverb artifact is to effectively lengthen the pulse of the transducer as each reverb echo become part of the main transducer pulse and thus any echoes received by the transducer.

Figure 3:
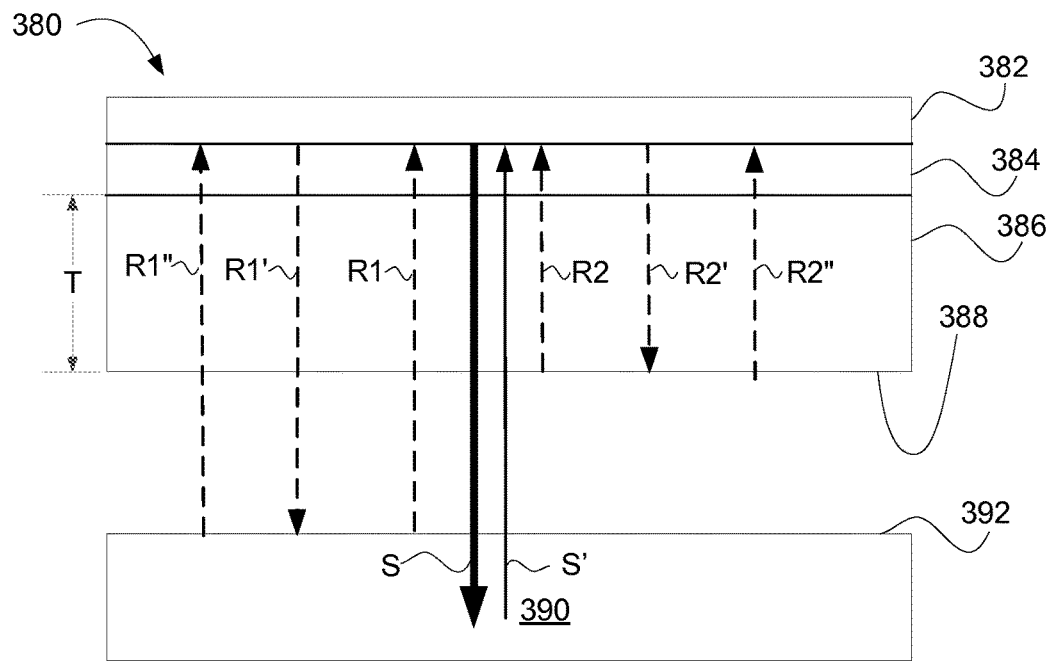
FIG. 3 is a schematic side view of a prior art transducer.

FIG. 3 is a schematic view of a prior art transducer 380 that illustrates one example of the intra-lens reflections and reverberation artifacts described above. The transducer 380 includes a transducer layer 382, a matching layer 384 and an acoustic lens 386 having a lower surface 388 and a thickness T. The transducer 380 transmits and receives ultrasound energy (e.g., high frequency ultrasound of 15 MHz or greater) through a skin line 392 of a subject 390 (e.g., a human patient, an animal). The transducer layer 382 is configured to transmit a primary ultrasound signal S into the subject 390 and receives ultrasound echoes S', which are used to form an ultrasound image.

First, second and third reflections R1, R1' and R1" illustrate one example of the multipath artifacts described above. The skin line 392 reflects a portion (e.g., 5%, 10%, 20%) of the signal S thereby forming the first reflection R1. The first reflection R1 propagates back toward the transducer layer 382, which reflects a portion (e.g., 5%, 10%, 20%) of the first reflection R1 back toward the subject thereby forming the second reflection R1'. The skin line 392 reflects a portion of the second reflection R1' back toward the transducer layer 382 thereby forming the third reflection R1". The transducer layer 382 receives the echoes S' along with portions of the first reflection R1 and third reflection R1", all of which are combined by an image processor (not shown) to form an ultrasound image. As those of ordinary skill in the art will appreciate, the reflections R1 and R1" can cause undesirable artifacts in the ultrasound image.

First, second and third reflections R2, R2' and R2" illustrate one example of the intra-lens reverberation artifacts described above. The lower surface 388 of the lens 386 reflects a portion (e.g., 5%, 10%, 20%) of the signal S thereby forming the first reflection R2. The first reflection R2 propagates back toward the transducer layer 382, which reflects a portion (e.g., 5%, 10%, 20%) of the first reflection R2 back toward the subject thereby forming the second reflection R2'. The lower surface 388 of the lens 386 reflects a portion of the second reflection R2' back toward the transducer layer 382 thereby forming the third reflection R2". The transducer layer 382 receives a combination of the echoes S' along with portions of the first reflection R2 and the third reflection R2" to form an ultrasound image. The reflections R2 and R2" can cause undesirable artifacts in the ultrasound image. In many instances, reflections similar to R1, R1", R2 and R2" can cause artifacts in the same ultrasound image, which can significantly reduce image quality.

Figure 4:
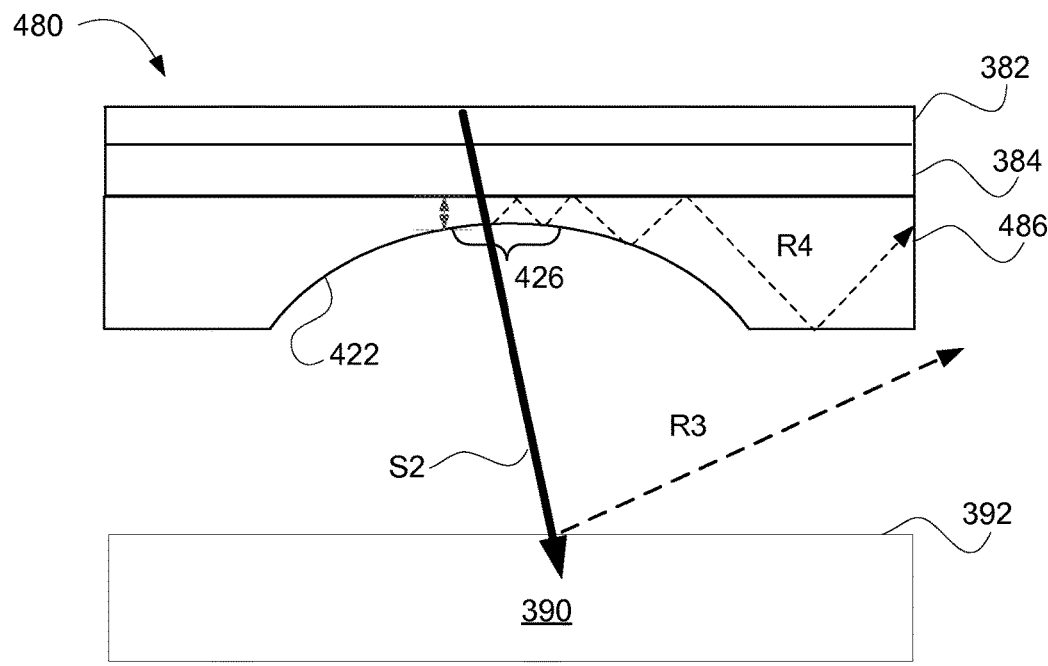
FIG. 4 is a schematic side view of a transducer configured in accordance with one or more embodiments of the disclosed technology.

FIG. 4 is a schematic side view of a transducer 480 configured in accordance with one or more embodiments of the disclosed technology. The transducer 480 includes an lens 486 having a curved surface 422 and a center portion 426. The center portion 426 has an average thickness approximately equal to an odd multiple of a quarter wavelength (e.g., ¼-wavelength, ¾-wavelength, 5/4-wavelength, 7/4-wavelength) of the center frequency of the transducer 480. A signal S2 is transmitted into the subject 390. The skin line 392 reflects a portion of the signal S2 to form a first reflection R3, and the curved portion 422 reflects a portion of the signal S2 to form second reflections R4. In contrast to reflections R1 and R2 discussed above, the first reflection R3 and the second reflections R4 are not specular reflections and thus do not travel back to the transducer 382. Accordingly the lens 486 can significantly reduce artifacts in a HFUS image, such as the intra-lens and multipath reflections discussed above with reference to FIG. 3.

The disclosed technology can provide a reduction of multipath artifacts (e.g., intra-lens reverberation artifacts, external multi-bounce artifacts) in HFUS transducers described above. In one aspect of the present disclosure, an ultrasound transducer includes an acoustical lens in which a center portion of the lens (e.g., the thinnest part of the concave shape of the lens between two end portions of the lens) has a thickness of about a fractional portion of a wavelength of the transducer center frequency. In some embodiments, for example, the lens center portion can have an average thickness approximately equal to an odd multiple of a quarter wavelength (e.g., ¼-wavelength, ¾-wavelength, 5/4-wavelength, 7/4-wavelength) of the transducer center frequency (e.g., 15 MHz. 20 MHz., 25 MHz., 30 MHz.). Incorporating the lens described above onto an ultrasound transducer results in the central portion of the lens effectively adding an additional matching layer (e.g., a quarter wavelength matching layer) to the front of the transducer. The disclosed technology therefore provides a lens having reduced acoustic reflectivity to normal incident plane waves, thus mitigating multipath acoustic artifacts in the image, and reducing intra lens reverb artifacts as well. In some embodiments, for example, the disclosed technology can increase the transmission coefficient of an HFUS transducer lens from 85% to about 95%. Stated differently, the disclosed technology can reduce the reflection coefficient of an HFUS transducer lens from 15% to less than between 5% and 10% or less, thereby significantly increasing sensitivity of the HFUS transducer (e.g., an increase between 1 dB and 2.5 dB).

In another aspect of the disclosed technology, an ultrasound transducer stack includes a transducer layer and a lens layer. The transducer layer is configured to transmit ultrasound energy at a center frequency (e.g., 15 MHz. or higher). The lens layer has an upper surface underlying the transducer layer. At least a portion of the lens layer has a concave curvature in a direction normal to an axial direction of the transducer. A center portion of the lens layer has an average thickness that is substantially equal to an odd multiple (e.g., 1, 3, 5) of a ¼ wavelength of the center frequency of the transducer layer. In some embodiments, a matching layer is disposed between the lens layer and the transducer layer. In one embodiment, for example, the matching layer is attached to the lens layer by another matching layer that comprises cyanoacrylate. In some embodiments, the lens layer has an acoustic impedance substantially different (e.g., 10% different, 25% different, 50% different) than an acoustic impedance of water.

In yet another aspect of the disclosed technology, an ultrasound system includes an ultrasound imaging system coupled to an ultrasound transducer probe. The ultrasound transducer probe is configured to transmit ultrasound toward a subject and receive ultrasound energy from the subject. The transducer probe includes a lens layer and one or more transducer elements configured to operate at a center frequency (e.g., between about 15 MHz and about 60 MHz). A portion of the lens layer has a concave curvature in a direction normal to an axial direction of the transducer. A center portion of the concave curvature has an average thickness substantially equal to (e.g., within about 1%, within about 2%, within about 5%) an odd multiple (e.g., 1, 3, 5, 7, 9) of a ¼ wavelength of the center frequency of the one or more transducer elements. In some embodiments, a reflection coefficient of the lens layer is less than about 5%. In some embodiments, the reflection coefficient is between, for example, about 1% and 15%.

In still another aspect of the disclosed technology, a method of constructing an ultrasound transducer includes fabricating an acoustic lens layer and attaching or bonding the lens layer to a first matching layer operationally coupled to a transducer layer. The lens layer is fabricated to have a center curved section and two flat side sections. Fabricating the curved section includes fabricating a center portion having a midpoint and two endpoints such that the center portion has a first thickness at the midpoint and a second thickness at each of the two endpoints. An average of the first thickness and the second thickness is substantially equal to (e.g., within about 1%, within about 2%, within about 5%) an odd multiple of a ¼ wavelength (e.g., ¼-wavelength, ¾-wavelength, 5/4-wavelength) of the center frequency (e.g., between about 15 MHz and about 60 MHz) of the ultrasound transducer. In some embodiments, the method further includes bonding or attaching a second matching layer to the lens layer with the first matching layer such that the second matching layer is positioned between the first matching layer and the transducer layer. In some embodiments, the lens layer has a speed of sound significantly different (e.g., 100% different, 200% different) than a speed of sound in water.

In another aspect of the disclosed technology, an ultrasound transducer stack includes a transducer layer comprising one or more ultrasound transducer elements configured to operate at a center frequency of 15 MHz or greater (e.g., between about 15 MHz and about 60 MHz). The transducer stack further includes an acoustic lens having a rear surface attached to a matching layer operationally coupled to the transducer layer. A front surface of the acoustic lens includes two flat side sections and a center curved section extending therebetween in an elevation direction relative to the transducer stack. A first thickness of the center curved section in an axial direction relative to the transducer stack is less than an odd multiple of ¼-wavelength of the center frequency. The thickness of the center curved section increases outwardly a first distance in the elevation direction to an endpoint having a second thickness in the axial direction that is greater than an odd multiple of ¼-wavelength of the center frequency such that the average thickness in the axial direction of the center curved section between the midpoint and the endpoint is substantially an odd multiple of ¼-wavelength of the center frequency. In some embodiments, a length of the center curved section is twice the first distance. In some embodiments, the length of the center curved section is about 10% or less of a total length of the transducer stack in the elevation direction. In some embodiments, the first thickness is between about 95% and 99.5% of the odd multiple of the ¼-wavelength of the center frequency, and the second thickness is between about 100.5% and 105% of the odd multiple of the ¼-wavelength of the center frequency.

Suitable Systems

FIG. 1 is a schematic view of an ultrasound system 100 configured in accordance with an embodiment of the disclosed technology. The ultrasound system 100 includes an ultrasound probe 104 coupled to an image processing system 102 via a link 106 (e.g., a wire, a wireless connection). The probe 104 includes a transducer 110 (e.g., an HFUS stack). The transducer 110 can transmit ultrasound energy (e.g., HFUS energy) into a subject and receive at least a portion of the reflected ultrasound energy from the subject. The received ultrasound energy can be converted into a corresponding electrical signal and transmitted electrically to the image processing system 102, which can form one or more ultrasound images based on the received ultrasound energy.

Figure 2A:
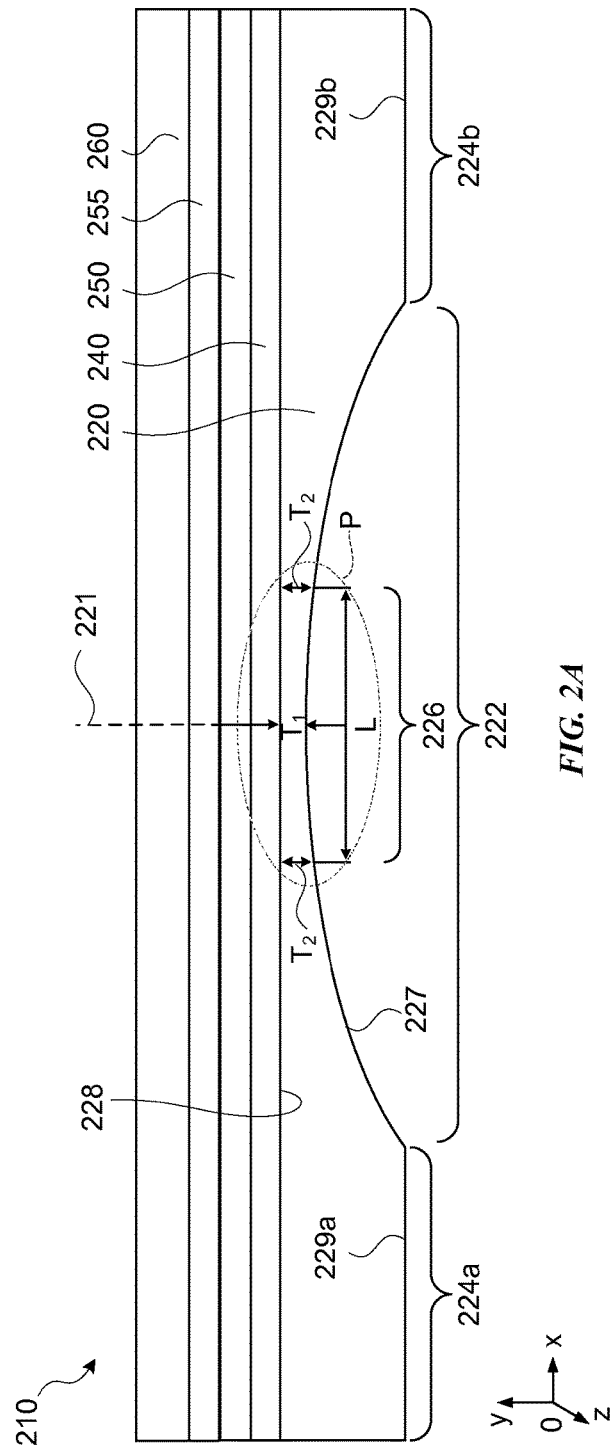
FIG. 2A is a cross-sectional schematic view of an ultrasound transducer stack configured in accordance with one or more embodiments of the disclosed technology.

FIG. 2A is a cross section schematic view of an ultrasound transducer stack 210 (e.g., the transducer 110 of FIG. 1) configured in accordance with one or more embodiments of the disclosed technology. The transducer stack 210 includes an acoustic lens 220, a first matching layer 240, a second matching layer 250, a third matching layer 255 and a transducer layer 260 (e.g., a piezoelectric transducer layer, a PMUT layer, a CMUT layer). In some embodiments, the first matching layer 240 can include a bonding material (e.g., cyanoacrylate, a polymer, an epoxy) having a ¼-wavelength thickness and can be configured to bond or otherwise attach a front surface of the second matching layer 250 to a rear surface 228 of the lens 220. A rear surface of the matching layer 250 is bonded or otherwise attached to a front surface of the third matching layer 255. A rear surface of the third matching layer 255 is attached to a front surface of the transducer layer 260. A centerline 221 extends along an axial direction (i.e., along the y-axis shown in FIG. 2A) of the transducer stack 210. In the illustrated embodiment, the transducer stack 210 includes a three matching layers—the first matching layer 240, the second matching layer 250 and the third matching layer 255. In some embodiments, however, the transducer stack 210 may include one or more additional matching layers as disclosed, for example, in U.S. Pat. No. 7,808,156, incorporated by reference above. Other embodiments of the transducer stack 210 may not include one or more of the first matching layer 240, the second matching layer 250 and the third matching layer 255.

The lens 220 includes a curved section 222 that has a concave curvature (e.g., cylindrical, parabolic or hyperbolic curvature) in an elevation direction (i.e., along the x-axis shown in FIG. 2) of the transducer stack 210. The curved section 222 is bounded by side section 224 (identified individually as a first side section 224a and a second side section 224b). The curved section 222 has a curved outer surface 227 and the flat side portions 224 have outer surfaces 229 (identified individually as a first outer surface 229a and a second outer surface 229b). The curved section 222 includes a center portion 226 centered at the centerline 221. As discussed in more detail with reference to FIG. 2A, the center portion 226 has a first thickness $T_1$ at a midpoint and a second thickness $T_2$ at two endpoints. The center portion 222 has a length L (e.g., less than 0.5 mm, 0.5 mm, 0.7 mm, 1 mm, greater than 1 mm) in the elevation direction of the transducer. In some embodiments, the length L can extend between about 1% and 10% of the length of the transducer in the elevation direction. In some embodiments, the length L and a radius of curvature of the center portion 226 can be determined by the focal number (e.g., F2, F5, F8, F10) of the lens and the focal depth of the transducer. As those of ordinary skill in the art will appreciate, the focal number of the lens is proportional to a ratio of the focal depth of the transducer and a length of the curved section 222 of the lens.

The lens 220 can comprise, for example, polymethylpentene, cross-linked polystyrene and/or polybenzimidazole. In other embodiments, however, the lens 220 can comprise any suitable material (e.g., metals, such as aluminum or stainless steel, or ceramic materials, such as PZT or alumina) having a speed of sound higher than a speed of sound of a medium being imaged (e.g., water, tissue in a subject). Moreover, in some embodiments, the first thickness $T_1$ of the center portion 226 may be slightly less than an odd multiple of ¼ of the wavelength (e.g., between approximately 95% and 99.5% of an odd multiple of the ¼ wavelength thickness) of a center frequency (e.g., 15 MHz or greater) of the transducer layer 260. Correspondingly, the second thickness $T_2$ may be slightly more than an odd multiple of ¼ of the wavelength (e.g., between approximately 100.5% and 105% of an odd multiple of the ¼ wavelength thickness) of the center frequency. The center portion 226 of the curved section 222 therefore has a substantially average thickness of approximately an odd multiple of ¼ of the wavelength (within a +/−5% of an odd multiple of ¼ wavelength). Fabricating the center portion 226 to have an average thickness substantially equal to a fractional wavelength of the center frequency of the transducer layer 260 can provide an improved acoustic match to a subject being imaged and therefore can significantly reduce multipath reflections compared to an acoustic lens having an arbitrary thickness.

Figure 2B:
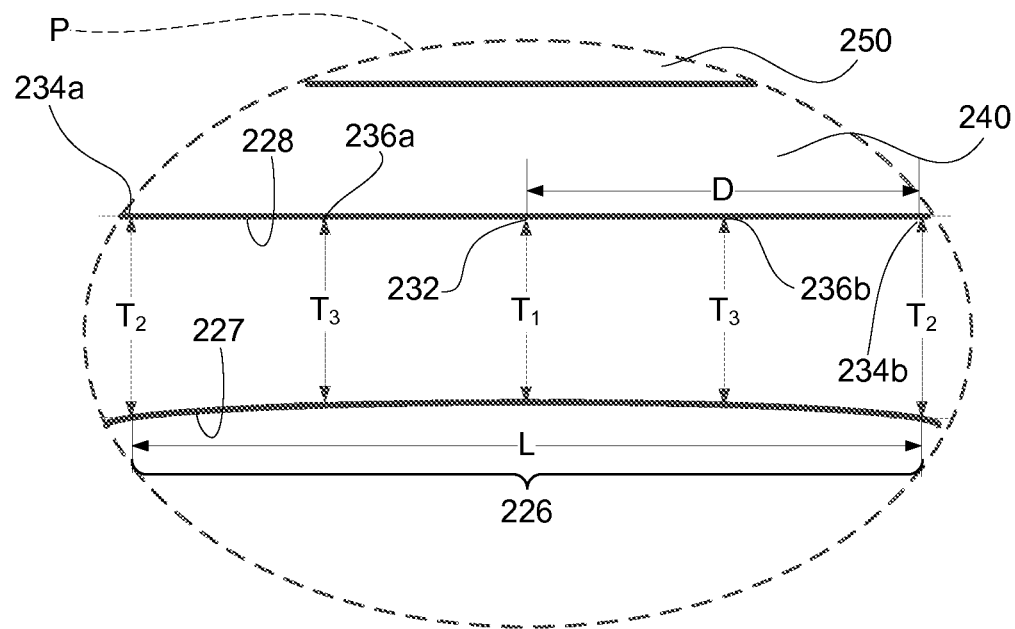
FIG. 2B is an enlarged view of a portion P of FIG. 2A.

FIG. 2B is an enlarged view of a portion P of FIG. 2A showing the center portion 226 in more detail. The center portion 222 has a midpoint 232 and extends between a first endpoint 234a and second endpoint 234b in the elevation direction. The midpoint 232 is spaced apart from each of the first and second midpoints 234a and 234b a distance D in the elevation direction (i.e., one-half the length L). The thickness of the center portion 222 in the axial direction increases outwardly from $T_1$ at the midpoint 232 to the thickness $T_2$ at each of the first and second midpoints 234a and 234b. The average thickness of the center portion 222 substantially equal to an odd multiple (e.g., 1, 3, 5, 7) of a ¼-wavelength of the center frequency of the transducer layer 260 (FIG. 2A) Further, at intermediate points 236a and 236b, the center portion 222 has a thickness $T_3$ generally corresponds to the average thickness of the center portion 222 between midpoint 232 and each of the first and second midpoints 234a and 234b.

In some embodiments, however, the center portion 226 can be configured to have an average ¾-wavelength thickness to provide adequate dielectric strength to meet desired medical electrical safety standards. In other embodiments, the center portion 226 may have an average thickness less than ¾ wavelength. In some embodiments, for example, the center portion 226 can be fabricated to have an average thickness of the ¼ of the wavelength of an operational center frequency (e.g., 20 MHz, 25 MHz, 30 MHz) of the transducer layer 260. In some embodiments, the average thickness of the center portion 226 can be any odd multiple (e.g., 1, 3, 5, 7, 9) of ¼ of the wavelength of the operational center frequency of the transducer layer 260 (FIG. 2A). In other embodiments, however, the average thickness can be any suitable fraction of the wavelength of the operational center frequency of the transducer layer 260 (FIG. 2A). Those of ordinary skill in the art will appreciate, for example, that for broadband ultrasound transducers, a ¼ wavelength lens thickness will generally perform better than a ¾ wavelength lens thickness, and increasing odd multiples of ¼-wavelength generally perform progressively worse. In contrast, narrowband transducers (e.g., CW Doppler transducers) can have acoustic lenses with increasing odd multiples of the ¼-wavelength without a significant reduction in performance.

Fabricating the center portion 226 to have of an average thickness corresponding generally to a fractional portion (e.g., ¼, ¾) of the wavelength can, in addition to minimizing multi-path artifacts, acoustically enhance a central part of the elevation dimension (i.e., along the x-axis of FIG. 2A) of the transducer layer 260 (FIG. 2A), thereby providing a desirable boost to a normal component of the elevation beam. This can be viewed as achieving the equivalent of mild apodization of the elevation beam by enhancing the central part of the beam relative to the edges, as opposed to attenuating the edges relative to the center of the beam. The apodization of the elevation beam can lead to a reduction in sidelobes in the elevation beam.

From the foregoing, it will be appreciated that specific embodiments of the invention have been described herein for purposes of illustration, but that various modifications may be made without deviating from the scope of the invention. Accordingly, the invention is not limited except as by the appended claims.

I claim:

1. An ultrasound transducer stack comprising:
   a transducer layer configured to transmit ultrasound energy at a center frequency;
   a lens layer secured to the transducer layer, wherein at least a portion of the lens layer has a concave recess with a length L measured in an elevation direction of the transducer stack and wherein a center portion of the concave recess has a length that is less than L and is defined between a center point of the concave recess and points outwardly therefrom in the elevation direction such that the center portion has an average thickness measured in an axial direction of the transducer stack that is substantially equal to one of 1, 3, 5 or 7 multiples of a ¼ wavelength of the center frequency of the transducer layer at a speed of sound in the lens material;

a first matching layer disposed between the transducer layer and the lens layer; and a second matching layer disposed between the lens layer and the first matching layer, wherein the second matching layer comprises cyanoacrylate, and wherein the first matching layer and the second matching layer each have a thickness approximately ¼-wavelength of the center frequency of the ultrasound energy from the transducer layer at the speed of sound in the lens material.

2. The ultrasound transducer stack of claim 1, wherein the center frequency at which the transducer layer is configured to transmit ultrasound energy is greater than 15 MHz, and wherein the lens layer is acoustically penetrable at frequencies greater than 15 MHz.

3. The ultrasound transducer stack of claim 1, wherein the average thickness of the center portion of the lens layer is ¼ of the wavelength of the center frequency of the ultrasound energy from the transducer layer at the speed of sound in the lens material.

4. The ultrasound transducer stack of claim 1, wherein the average thickness of the center portion of the lens layer is ¾ of the wavelength of the center frequency of the ultrasound energy from the transducer layer at the speed of sound in the lens material.

5. The ultrasound transducer stack of claim 1, wherein the lens layer has an acoustic impedance substantially different than an acoustic impedance of water.

6. An ultrasound system, comprising:

an ultrasound imaging system; and an ultrasound transducer probe coupled to the imaging system and configured to transmit ultrasound energy at a center operating frequency toward a subject and receive ultrasound energy from the subject, wherein the ultrasound transducer probe includes:

one or more transducer elements configured to generate ultrasound energy at the center operating frequency; and a lens layer, wherein at least a portion of the lens layer has a concave recess with a length L measured in an elevation direction of the transducer probe and a center region that is smaller than L measured in the elevation direction, wherein the average thickness of the lens in the center region as measured in an axial direction of the transducer probe is substantially equal to one of 1, 3, 5 or 7 multiples of ¼ wavelength of the center frequency of the ultrasound energy produced at a speed of sound in the lens layer.

7. The ultrasound system of claim 6, wherein the center operating frequency of the ultrasound energy transmitted is greater than 15 MHz, and wherein the lens layer is acoustically penetrable at frequencies greater than 15 MHz.

8. The ultrasound system of claim 7, wherein a reflection coefficient of the lens layer is less than 10%.

9. The ultrasound system of claim 6, wherein the average thickness of the center region of the lens layer is ¼ of the wavelength of the center frequency of the ultrasound energy transmitted.

10. The ultrasound system of claim 6, wherein the average thickness of the center region of the lens layer is ¾ of the wavelength of the center frequency of the ultrasound energy transmitted.

11. An ultrasound transducer stack, comprising:

a transducer layer comprising one or more ultrasound transducer elements configured to generate ultrasound energy at a center frequency of 15 MHz or greater;

a matching layer spaced apart from the transducer layer in an axial direction relative to the transducer stack; and an acoustic lens having a front surface and a rear surface, wherein the rear surface of the lens is attached to the matching layer, wherein the front surface includes two flat side sections and a concave curved section extending therebetween in an elevation direction relative to the transducer stack, wherein the concave curved section includes a central area that is smaller than a length of the concave curved section as measured in the elevation direction with a first thickness at a center of the lens in the axial direction of the stack that is less than one of 1, 3, 5 or 7 multiples of ¼-wavelength of the center frequency of the ultrasound energy generated at a speed of sound in the acoustic lens, wherein the thickness of the central area increases outwardly in the elevation direction to a pair of points where the thickness of the lens has a second thickness in the axial direction that is greater than said one of 1, 3, 5 or 7 multiples of ¼-wavelength of the center frequency of the ultrasound energy generated at the speed of sound in the lens such that the average thickness of the central area of the lens in the axial direction is substantially equal said 1, 3, 5 or 7 multiples of ¼-wavelength of the center frequency of the ultrasound energy generated by the transducer layer at the speed of sound in the lens.

12. The ultrasound transducer stack of claim 11, wherein the first thickness is between about 95% and 99.5% of said one of 1, 3, 5 or 7 multiples of the ¼-wavelength of the center frequency, and wherein the second thickness is between about 100.5% and 105% of said one of 1, 3, 5 or 7 multiples of the ¼-wavelength of the center frequency of the ultrasound energy generated.

13. An ultrasound transducer comprising:

a transducer layer configured to generate ultrasound energy at a center frequency; and a lens layer coupled to the transducer layer, wherein the lens layer has a concave curvature in a direction normal to an axial direction of the transducer having a length L measured in an elevation direction of the transducer, and a center portion of the lens layer that is smaller than L with a central point where a thickness of the lens layer as measured in an axial direction of the transducer is between 95%-99.5% of one of 1, 3, 5 or 7 multiples of a ¼ wavelength of the center frequency of the ultrasound energy generated at a speed of sound in the lens layer and extending outwardly to points where the thickness of the lens layer is between 100.5 and 105% of said one of 1, 3, 5 or 7 multiples of a ¼ wavelength of the center frequency of the ultrasound energy generated at the speed of sound in the lens layer such that an average thickness of the lens layer in the center portion of the lens is substantially equal to said one of 1, 3, 5 or 7 multiples of the ¼ wavelength of the center frequency of the ultrasound energy generated by the transducer.

* * * * *